United States Patent [19]

Chen

[11] Patent Number: 5,155,264
[45] Date of Patent: Oct. 13, 1992

[54] PROCESS FOR PREPARING GLYCINE IN HIGH YIELD

[75] Inventor: Ming F. Chen, Taichung, Taiwan

[73] Assignee: Hakko Tsusho CO., Ltd., Tokyo, Japan

[21] Appl. No.: 715,965

[22] Filed: Jun. 17, 1991

[30] Foreign Application Priority Data

Sep. 4, 1990 [JP] Japan .................................. 2-234038
Oct. 16, 1990 [JP] Japan .................................. 2-275421

[51] Int. Cl.⁵ .......................................... C07C 229/00
[52] U.S. Cl. .................................................. 562/575
[58] Field of Search ...................................... 562/575

[56] References Cited

U.S. PATENT DOCUMENTS 3,190,194  6/1965  Williams ............................... 562/575

Primary Examiner—Michael L. Shippen
Attorney, Agent, or Firm—Sherman and Shalloway

[57] ABSTRACT

Desclosed is a process for preparing glycine in a high yield, which comprises reacting a carboxymethyl quaternary ammonium chloride represented by the following structural formula (I):

$$Cl(R_3NCH_2COOH) \qquad (I)$$

wherein R represents an alkyl group having 1 to 4 carbon atoms, with an aminomethanol derivative represented by the following structural formula (II):

$$\underset{HO.CH_2NH}{\overset{R_1}{|}} \qquad (II)$$

wherein $R_1$ represents a hydrogen atom or a $CH_2OH$ group, in a solvent.

11 Claims, 8 Drawing Sheets

PROCESS FOR PREPARING GLYCINE IN HIGH YIELD

BACKGROUND OF THE INVENTION

1. Field of the Invention

The present invention relates to a process for preparing glycine. More particularly, the present invention relates to an improvement in the process for preparing glycine in a short time by one stage reaction of a carboxy-methyl quaternary ammonium chloride, formed by reaction of monochloroacetic acid (hereinafter abbreviated to "MCA") with a tertiary amine, with an aminomethanol derivative (glycolloamine, methylolamine or hydroxymethylamine), formed by reaction of ammonia with formaline, in an aqueous solution, an alcohol solution or a mixed solution of both.

2. Description of the Related Art

Glycine (monoaminoacetic acid) is an amino acid which is most popularly used as an additive to processed foods for improving the taste and flavor and prolonging the storage period, a starting material for the synthesis of agricultural chemicals, a starting material for the synthesis of medicines, a starting material for the synthesis of other amino acids and an agent for preventing decomposition of vitamin C.

Glycine has heretofore been synthesized mostly according to the Strecker process in which aminoacetonitrile is synthesized by the ammonosis of glycollonitrile and the aminoacetonitrile is further hydrolyzed, but the process using MCA as the starting material is a classic bench-scale process which is considered to be economically disadvantageous. The reasons are as follows.

1) Since iminodiacetic acid and nitrilotriacetic acid are formed as by-products in addition to glycine by the reaction, the yield is low.

2) A large quantity of ammonia should be used.

3) The reaction time is long and it takes several days to complete the reaction at room temperature.

These defects are point out in Organic Synthesis, volume 1, page 300.

Various processes have been proposed and investigations have been published for overcoming these defects (see, for example, U.S. Pat. No. 3,190,914 (Jan. 22, 1965) and Japanese Examined Patent Publication No. 58-22055).

It is taught in the above U.S. patent that glycine is obtained in a yield of 80 to 90% by reacting MCA in an aqueous solution with an aminomethanol derivative produced by reaction of aqueous ammonia with a formalin solution. However, when this process is worked on a commercial scale, the following defects are observed. In case of the equimolar reaction, a long time is required and the yield is as low as 70%, and in order to elevate the yield to 90%, ammonia should be used in an amount of at least 3 moles per mole of MCA. Under this condition, however, excessive ammonia is bonded with hydrochloric acid formed by the reaction to form ammonium chloride and the operation of separating glycine after the reaction is rendered difficult, and for complete separation of glycine, such operations as concentration and crystallization utilizing the difference of the solubility between glycine and ammonium chloride should be performed repeatedly. The loss of glycine by this repetition of these operations is large, resulting in reduction of the yield.

In the process disclosed in Japanese Examined Patent Publication No. 58-222055, large quantities of ammonium carbonate and ammonium chloride are used for preventing formation of by-products, but a diacetic acid is still formed during the reaction, and the amount of used aqueous ammonia is more than 10 times the amount formed of glycine and the productivity per unit volume of the reactor is considerably low.

Furthermore, there is known a process in which a hexamine (hexamethylenetramine) is used instead of ammonia. Also in this process, the conversion is as low as about 70 to about 80%, and the separation of glycine after the reaction is inhibited by the hexamine having a low solubility.

SUMMARY OF THE INVENTION

It is therefore a primary object of the present invention to overcome the foregoing defects of the conventional processes and provide a process in which glycine having a high purity is prepared from MCA as the starting material in a high yield.

More specifically, in accordance with the present invention, there is provided a process for preparing glycine in a high yield, which comprises reacting a carboxymethyl quaternary ammonium chloride represented by the following structural formula (II):

wherein R represents an alkyl group having 1 to 4 carbon atoms,
with an aminomethanol derivative represented by the following structural formula (II):

wherein $R_1$ represents a hydrogen atom or a $CH_2OH$ group,
in a solvent.

The above reaction can be carried out under atmospheric pressure or elevated pressure at a temperature lower than the boiling point of the solvent under the reaction pressure.

The above reaction is characterized in that the carboxymethyl quaternary ammonium chloride formed by reacting monochloroacetic acid with a tertiary amine having 1 to 4 carbon atoms in water or an inert organic solvent is used.

According to the process of the present invention, at first, MCA is reacted with a tertiary amine in an aqueous solution to form a carboxymethyl quaternary ammonium chloride and to increase the activity by ionizing Cl of MCA, and the carboxymethyl quaternary ammonium chloride is then reacted with an aminomethanol derivative formed by reaction of ammonia or aqueous ammonia with a formalin solution to selectively form glycine (aminoacetic acid), whereby glycine can be obtained easily in such a high yield as not attainable by the conventional techniques.

As the reaction solvent, there can be used an aqueous solvent, an alkyl alcohol solvent or a mixture of both.

Furthermore, a reaction product of ammonia with formalin or paraformaldehyde can be used as the above-mentioned derivative.

According to a preferred embodiment of the process of the present invention, the reaction between the above-mentioned carboxymethyl quaternary ammonium chloride and the above-mentioned derivative is continuously carried out by using a reactor of the interior path heating type having a reaction filler in the interior thereof. In this case, the temperature of the reactor can be maintained at 40° to 80° C.

DETAILED DESCRIPTION OF THE PREFERRED EMBODIMENTS

Figure 1:
FIG. 1 is a chart showing the infrared absorption spectrum of standard glycine.

The present invention will now be described in detail.

(A) Reaction Mechanism

The mechanism of the preparation process of the present invention comprises preliminary reactions (1) and (2) and basic reaction (3) described below.

(1) Formation of Carboxymethyl Quaternary Ammonium Chloride by Reaction between MCA and Tertiary Amine (represented by formed R$_3$N)

This reaction is represented by the following reaction formula:

$$Cl \cdot CH_2COOH + R_3N \rightarrow Cl^- [R_3NCH_2COOH]^- \quad (A)$$

In an aqueous solution, the reaction product is ionized.

(2) Synthesis of Aminomethanol Derivative by Reaction between Ammonia (or Aqueous Ammonia) and Formalin The reaction is represented by the following reaction formula:

$$NH_4OH + NCHO \rightarrow HOCH_2NH_2 + H_2O \quad (B)$$

At a higher reaction temperature, dimethyl alcohol and trimethyl alcohol derivatives are formed.

(3) Formation of Glycine by Reaction between Above-Mentioned Two Reaction Products This reaction is represented by the following reaction formula:

a) $Cl^-[R_3NCH_2COOH]^+ + H_2N \cdot CH_2OH$
$\rightarrow HO \cdot CH_2NHCH_2COOH + R_3N \cdot HCl \quad (C)$ or $Cl^-[R_3NCH_2COOH]^- + HN(CH_2OH)_2 \rightarrow$
$(HO \cdot CH_2)_2NCH_2COOH + R_3N \cdot HCl \quad (D)$ b) $R_3N \cdot HCl \rightleftharpoons R_3N + HCl \quad (E)$ c) $HO \cdot CH_2 \cdot NH \cdot CH_2COOH$ or 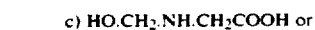

$(HO \cdot CH_2)_2NCH_2COOH \xrightarrow{\Delta}{Ca + HCl}$ 

$H_2N \cdot CH_2 \cdot COOH + HCHO$

In the basic reaction (3), MCA is first reacted with a tertiary amine to form a carboxymethyl quaternary ammonium chloride, whereby Cl is ionized and the activity is increased, and this activated Cl is readily reacted with N$^+$ proton of the —NH$_2$ group of the aminomethanol derivative to form HCl. HCl is bonded with the tertiary amine set free to form a tertiary amine hydrochloric acid [formula (E)]. The reaction product, that is, methylolglycine or dimethylolglycine, is decomposed to glycine and formaldehyde presumably by the catalytic action of HCl of the formed tertiary amine hydrochloric acid salt [formula (F)].

The above reaction is advanced substantially quantitatively and glycine alone is selectively formed, and formation of by-products that can hardly be separated, such as imino-diacetic acid and nitrilotriacetic acid, which is the serious problem of the conventional technique, can be controlled below 1% (confirmed by HPLC).

For this reaction, an aqueous solvent, an alcoholic solvent or a mixture thereof can be used. In the case where an aqueous solvent is used, glycine formed by the reaction of formula (F) is dissolved in water, and since each of reactions (A) through (D) is an ionizing reaction, the conversion of glycine based on MCA is substantially 100%. Moreover, since the amount of the by-product that can hardly be separated is small, as mentioned above, formed glycine can be easily recovered by addition of an alcohol or the like. In the case where an alcoholic solvent is used, glycine is precipitated in a substantially pure state simultaneously with the formation, and therefore, glycine can be obtained by one-stage reaction. In this case, the ammonium chloride of the tertiary amine (the tertiary alcohol amine having 1 to 4 carbon atoms) is dissolved in the alcohol and is completely separated from glycine.

Incidentally, in the case where the solvent is a mixed solvent of water and an alcohol, the conversion based on MCA is not different from the conversion obtained in case of the aqueous solvent, though the amount precipitated of glycine is changed.

The preparation process of the present invention will now be described with reference to the alcoholic solvent and the aqueous solvent, respectively.

(B) Alcoholic Solvent

The preliminary reaction is conducted for the synthesis of the carboxymethyl quaternary ammonium chloride. This product can be obtained substantially in a theoretical yield by heating MCA and a tertiary amine in an alcohol or other inert solvent. The reaction product is soluble in an alcohol.

The aminomethanol derivative is called "glycolloamine", "methylolamine" or "hydroxymethylamine", and the derivative can be obtained in the form of a transparent liquid by forming a slurry of paraformaldehyde in an alcohol and possessing a slight excess of ammonia into the slurry at a temperature lower than 50° C., preferably lower than 20° C.

The reaction product is composed mainly of an aminomonomethanol derivative, but as the reaction temperature is elevated, the reaction product comes to include an aminodimethanol derivative. A mixture of both the derivatives and a reaction product composed solely of the aminodimethanol derivative can be used, but it is preferred that the reaction product be used in the form of an aminomonomethanol derivative.

At the reaction, the former reactant is used in the form of an alcohol solution and, if necessary, the alcohol solution is heated. Then, an alcohol liquid of the aminomethanol derivative is added dropwise or at a time to the above alcohol solution and the mixture is heated. Glycine is immediately formed as a crystalline precipitate and a slurry is obtained. After confirmation of disappearance of the peak of MCA by HPLC, the reaction is stopped and the slurry is filtered to recover glycine. Instead of this reaction, there can be adopted a method of obtaining a precipitate of glycine by dissolving paraformaldehyde in a tert-amine/monochloroacetic acid reaction liquid and passing ammonia into the solution. In this case, the yield is surprisingly increased to at least 95%. This reaction is described in detail in Examples 1-11 and 1-12 given hereinafter.

The alcoholic solvent used in the process of the present invention is required to have such a property that the alcoholic solvent should dissolve therein the starting aminomethanol derivative and carboxymethyl quaternary ammonium chloride and the tertiary amine hydrochloric acid salt formed but cannot dissolve glycine therein. From this viewpoint and the economical viewpoint, an alcohol having 1 to 4 carbon atoms, which can be easily handled, is preferably used. This alcohol is also advantageous in that the alcohol can dissolve the aminomethanol derivative in the heated state but at a low temperature, the solubility is low and the majority of the aminomethanol derivative is precipitated as a crystal and can be recovered. Therefore, the used aminomethanol can be recovered and re-used in next run, and the starting material cost can be drastically reduced.

As the alcohol having 1 to 4 carbon atoms, there can be mentioned methanol, ethanol, n-propanol, isopropanol, n-butanol, isobutanol and tert-butanol.

Furthermore, glycine is not soluble in the alcohol having 1 to 4 carbon atoms, in the other hand, other products or unreacted substances are completely dissolved in the alcohol, and the intended product can be obtained in the form of a crystal. This is another advantage attained by the use of the alcohol having 1 to 4 carbon atoms. The solubility of glycine in the alcohol is about 1% even in the state where the alcohol contains about 40% of water. Accordingly, in the case where certain reduction of the yield is not a serious problem, the alcohol can be used in a water-containing state in the process of the present invention.

Trialkylamine (Tertiary Amine)

The trialkylamine used in the process of the present invention is a tertiary amine having an alkyl group having 1 to 4 carbon atoms. This tertiary amine takes the following important roles in the present reaction.

(1) By reaction with monochloroacetic acid, the trialkylamine forms a trialkylcarboxymethyl ammonium chloride to increase the reaction activity of Cl and simultaneously, the trialkylamine absorbs HCl formed by the reaction in a moment to form a trialkylamine hydrochloride, whereby formation of ammonium chloride, which is an impurity that can hardly be separated, by reaction of $NH_3$ with HCl can be prevented.

(2) Methylolglycine as the reaction product is decomposed into glycine and formaldehyde by the catalytic action of hydrochloric acid of the trialkylamine hydrochlrode formed by the reaction, and glycine is precipitated as a crystal. Accordingly, in this process, ammonium chloride is not formed and glycine can be easily separated.

It may be considered that an amine having a pyridine nucleus can be used as the terticary amine. However, pyridine reacts with monochloroacetic acid and is generally decomposed at a temperature higher than 60° C. while generating carbon dioxide gas and forming N-methylpyridinium chloride, and hence, a trialkylcarboxymethyl ammonium chloride is not formed.

Glycine is similarly formed even if this reaction of the trialkylcarboxymethyl ammonium chloride is carried out in another inert solvent such as benzene, toluene, xylene, hexane or heptane and the reaction product is then dissolved in water or an alcohol having 1 to 4 carbon atoms.

However, if a trialkylamine is dropped into the mixture solution of the aminomethanol derivative and monochloroscetic acid without passing through the above-mentioned reaction, not only the yield but also the purity is reduced.

A trialkylamine having an alkyl group having 1 to 4 carbon atoms can be used as the trialkylamine. Triethylamine, tripropylamine and tributylamine are practically preferably used.

Molar Ratios of Starting Materials

If only occurrence of the reaction between MCA and the aminomethanol derivative is intended, the reaction ratio between the reactants is not particularly critical but optional. However, in order to completely react MCA, it is preferred that the MCA/aminomethanol derivative molar ratio be 1/at least 1. Namely, it is preferred that the aminomethanol derivative be used in an amount of at least 1.5 moles per mole of MCA and MCA be completely reacted within a short time.

This molar ratio is preferably 1.0/at least 2.0, but if the molar ratio is within the range of from 1/1.5 to 1/2.0, a yield of at least 95% is attained within a short time. Preferably, the aminomethanol derivative is used in a state where ammonia is slightly excessive.

In the case where MCA is substantially reacted, formaldehyde left in the filtrate after separation of glycine is present in the form of aminomonomethanol and aminodimethanol and is in the dehydrated form of $(CH_2)_m N_n$ (in which m and n represent an integer) at a temperature of at least 60° C., and therefore, the formaldehyde is precipitated by cooling and is recovered and used again.

Solvent and Amount Used Thereof

In the process of the present invention, the alcohol having 1 to 4 carbon atoms is used mainly for the synthesis of the aminomethanol derivative, the reaction between monochloroacetic acid and the trialkylamine, and the formation of glycine. At the synthesis of the aminomethanol derivative, the alcohol is used in an amount at least 1.5 times, preferably 1.5 to 2.0 times, the amount used of the starting material. At the monochloroacetic acid-trialkylamine reaction, the amount of the alcohol is 1.0 to 3.0 times, preferably 1.0 to 2.0 times. At the final formation, the amount of the alcohol is 1.0 to 3.0 times, preferably 1.0 to 2.5 times. As the amount used of the alcohol is increased, the volume becomes large and no economical advantage is attained, but as the amount of the alcohol is small, formation of impurities becomes conspicuous.

An anhydrous alcohol not containing water is preferably used as the alcohol, but even a water-containing alcohol can be used. An alcohol containing about 40% of water can dissolve about 1.0% of glycine and the yield is correspondingly reduced.

The solubility of glycine in a water-free alcohol (having a water content lower than 0.1%) is lower than 0.5% at 50° C., but practically, the amine hydrochloride, the aminomethanol derivative and the like are present in the dissolved state but no peak of glycine is observed at the HPLC test.

If filtration is carried out at a temperature higher than 40° C. after completion of the reaction, only glycine is precipitated but all of other impurities are dissolved in the alcohol and no peak of glycine is observed at HPLC of the filtrate.

Reaction Temperature and Pressure

At a temperature higher than 30° C., the speed of the reaction between the aminomethanol derivative and the carboxymethyl quaternary ammonium chloride is increased with elevation of the temperature. If the temperature is lower than the boiling point of the solvent, the above-mentioned object is substantially attained. However, if the boiling point of the solvent is elevated by elevating the pressure, the reaction temperature can be further elevated. The reaction temperature is preferably 30° to 80° C., especially preferably 50° to 80° C. If the reaction temperature is within this range, the reaction time is several minutes to 8 hours. If the reaction temperature is higher than 80° C., formation of impurities becomes conspicuous with elevation of the temperature. If the reaction temperature is lower than 30° C., the reaction speed is reduced with dropping of the temperature, and at 20° C., the reaction is completed for about 4 days. Accordingly, if the reaction temperature is lower than 30° C., the process becomes economically disadvantageous.

Reaction Time

The reaction time depends on the molar ratio of the starting materials and the reaction temperature, and influences of the reaction temperature are large, and the following test results were obtained.

| Reaction Temperature | Reaction Time |
| --- | --- |
| 20° C. | about 4 days |
| 30° C. | about 50 hours |
| 40° C. | about 16 hours |
| 50° C. | 7 to 10 hours |
| 55° C. | 6 to 7 hours |
| 60° C. | 2 to 3 hours |
| 65° C. | 1.5 to 2 hours |
| 70° C. | 1 to 1.5 hours |

The foregoing data are those obtained when the monochloroacetic acid/aminomethanol derivative molar ratio is in the range of from 1.0/1.5 to 1.0/2.0. If the molar ratio of the aminomethanol derivative is increased, the reaction time can be shortened. At a temperature higher than 65° C., formation of impurities becomes conspicuous with elevation of the temperature, resulting in reduction of the yield and purity. This fact can be confirmed by HPLC.

Filtration and Washing

Preferably, the reaction liquid where the reaction has been completed is filtered at a temperature higher than 40° C. The filtration can be carried out under pressure or in vacuo or by centrifugal filtration. After the filtration, the recovered crude crystal is rinsed and washed with a warm alcohol, and by washing away the impurities adhering to the surface of the crude crystal completely, the purity can be elevated to a desired level.

The purity of the unwashed crude crystal is about 90%, and the solubility of glycine in the alcohol is about 0.5% at 50° C. Glycine is not substantially lost by washing. The washing liquid can be used for the reaction of the next cycle.

The filtrate left after separation of the crude crystal comprises free paraformaldehyde, an aminomethanol derivative (an aminomonomethanol derivative/aminodimethanol derivative mixture) and a trialkylamine hydrochloride, and if the filtrate is cooled, paraformaldehyde and the aminomethanol derivative are recovered as crystals in yields higher than about 80% but the trialkylamine is left in the solution in the form of a hydrochloride. By adding NaOH to the solution, the trialkyamine is substantially recovered.

Confirmation and Identification of Glycine as Product

The reaction states at respective steps of the reaction can be confirmed by HPLC, and glycine as the product is confirmed and identified by the melting point (M.P.), $^{13}$C-NMR, $^{1}$H-NMR, infrared absorption spectrum (IR) and elementary analysis. Furthermore, for the analysis of the purity, titration by the perchloric acid method and HPLC determination are performed.

(C) Aqueous Solvent

The carboxymethyl quaternary ammonium chloride is obtained in the form of an aqueous solution by dissolving MCA in water and gradually adding a tertiary amine to the solution. Since the reaction is exothermic, if the tertiary amine is added at a time, the temperature rises to the boiling point. The reaction temperature is preferably lower than 70° C. It also is preferred that the tertiary amine be added in an amount larger than the theoretical amount and MCA be completely reacted. Furthermore, as in the case where the alcoholic solvent is used, there can be adopted a method in which the reaction is carried out in an aqueous medium and the reaction product is used in the state dissolved in water.

The aminomethanol derivative can be prepared by adding aqueous ammonia, for example, 28% aqueous ammonia, or introducing gaseous ammonia into a formalin solution, for example, a commercially available 37% formalin solution, at a temperature lower than 20° C. The point of completion of the reaction is confirmed by HPLC, and when ammonia is added until the pH value exceeds 9.0, the product is composed of the aminomonomethal derivative and formation of an animodimethanol derivative and aminodimethanol derivative can be avoided. If the reaction temperature is not lower than 50° C., especially not lower than 20° C., a side reaction, for example, dehydration reaction, is caused and no good results can be obtained.

An aqueous solution of this aminomethanol derivative is added to a solution of an MCA/tertiary amine reaction product at a time or dividedly. Heat is generated and the reaction is advanced, and if the temperature is in the range of 40° to 70° C., glycine is formed for 10 and odd minutes to 3 hours. At 70° C., the reaction is completed substantially in a moment, and if the reaction is conducted for a long time, the aminomethanol derivative undergoes deamination and the di- or tri-methanol derivative is formed, and at a higher temperature, dehydration is caused and $(CH_2)_m N_n$ (in which m and n represent an integer) is formed and singled in glycine. Therefore, it is preferred that the reaction be carried out at a temperature as low as possible. The advance of the reaction can be traced by HPLC. The reaction is completed when the peak of MCA becomes smaller than 0.5%.

The solvent used in the process of the present invention is water, and use of water as the solvent is advantageous in the following point. More specifically, Cl of the carboxymethyl quaternary ammonium chloride formed by the reaction between MCA and the tertiary amine is more easily ionized than when an alcoholic solvent is used, and the activity is elevated and the Cl ion effectively attacks the opponent $H^+$ proton. The reaction is completed almost in a moment and the conversion is substantially 100%.

Reaction Temperature, Reaction Pressure, Molar Ratios of Starting Material and Trialkylamine (Tertiary Amine)

These conditions are substantially the same as those described above with respect to the alcoholic solvent.

Solvent and Amount Used Thereof

Preferably, the amount of the aqueous solvent is 1.0 to 3.0 times, especially 1.0 to 2.0 times, the amount of the reactants. At the reaction of forming the aminomethanol derivative, it is preferred that 28% aqueous ammonia be used in an amount of 1.0 to 1.5 moles per mole of the formalin solution. When a mixture of the aqueous solvent and alcoholic solvent is used, glycine is precipitated according to the mixing ratio between the two solvents and glycine having a high purity can be obtained.

Reaction Time

The reaction time depends greatly on the molar ratios of the starting materials and the reaction temperature. Influences of the reaction temperature are large, and the following test results were obtained.

| Reaction Temperature | Reaction Time |
|---|---|
| 40° C. | about 3 hours |
| 50° C. | about 2 hours |
| 60° C. | about 1 hour |
| 70° C. | about 0.5 hour |
| 80° C. | several minutes |

Treatment after Glycine Synthesis Reaction

After completion of the synthesis of glycine by the reaction between the carboxymethyl quaternary ammonium chloride and the aminomethanol derivative, the entire reaction mixture is subjected to evaporation to dryness, and an alkyl alcohol having 1 to 4 carbon atoms is added to the solid and the mixture is stirred to dissolve all of by-products other than glycine completely in the alcohol. Since glycine is hardly dissolved in the hot alkyl alcohol, if the mixture is rinsed, washed and filtered by using the hot alkyl alcohol, crude glycine having a purity higher than 98% in a substantially theoretical yield is obtained in the form of a white crystalline powder.

As the alkyl alcohol having 1 to 4 carbon atoms, there can be used methyl alcohol, ethyl alcohol, propyl alcohol, isopropyl alcohol, n-butyl alcohol, isobutyl alcohol and tertiary butyl alcohol.

Application to Continuous Reaction

When an aqueous solvent is used, the reaction temperature can be in the range of from room temperature to the boiling point of the solvent, and as the temperature is elevated, the reaction speed is increased. At 80° C., the reaction is completed substantially in a moment, and at 60° C., the reaction is completed within 1 to 2 minutes. If the molar ration of ammonia to formaldehyde is higher than 0.5 moles, formation of the iminodiacetic acid can be controlled.

A pipe type reactor can be used as the continuous reactor, and in order to increase the contact efficiency, it is preferred that an appropriate filler and a distributor for dispersing the reactants be disposed in the reactor. A high temperature is necessary for completing the reaction within several minutes, and it is preferred that the reaction temperature by 40° to 80° C., especially 70° to 80° C. If this temperature is adopted in the batchwise method, the high-temperature reaction should be conducted for a long time and formation of impurities becomes conspicuous. However, in the continuous method, this trouble is not caused and glycine can be obtained at a conversion of almost 100% based on MCA.

EXAMPLES

The present invention will now be described in detail with reference to the following examples.

Example 1-1

In 100 cc of methanol was suspended 30 g of paraformaldehyde, and ammonia gas was passed through the suspension. The reaction temperature was maintained at 20° C., and when the liquid became transparent, supply of ammonia gas was stopped. The amount used of ammonia gas was about 19 g.

Then, 47.25 g of monochloroacetic acid was dissolved in methanol, and when 50.5 g triethylamine was added, exothermic reaction was gradually advanced. While maintaining the final temperature at 60° C., the liquid of the aminomethanol derivative formed from paraformaldehyde and ammonia gas was added to the reaction liquid, and the mixture was stirred at a temperature of 60°±2° C. Immediately, a precipitate was formed and the liquid became opaque to form a slurry. When the peak of monochloroacetic acid disappeared at the HPLC examination, the reaction was stopped. The time required for the reaction was about 3 hours. The reaction liquid was immediately filtered (at a temperature maintained above 40° C.). The residual crude crystal was rinsed two times with 20 cc of warm methanol, and was then washed and dried.

Amount Obtained: 35.5 g.
Purity: 98.5% (titration method and HPLC).
Yield: 93.2%.
M.P.: 226° to 229 ° C. (decomposition started at 226° C.).

| | Elementary Analysis Values: | | |
|---|---|---|---|
| | C | H | N |
| Found values | 31.94 | 6.67 | 18.60 |
| Theoretical Value | 32.00 | 6.71 | 18.66 |

Figure 2:
FIG. 2 is a chart showing the infrared absorption spectrum of glycine obtained in Example 1-1.

Results of IR Measurement (KBr tablet, IRDC-78) (see FIGS. 1 and 2): 3225~2600: $\nu'N—H_3$. ~2890: $\nu CH$. 1598: $\nu C=O$ of COO— (asymmetric). 1522: $\delta^+N—H_3$. 1413: $\nu C=O$ of COO— (symmetric). 1334: $\nu C—N$.

Figure 3:
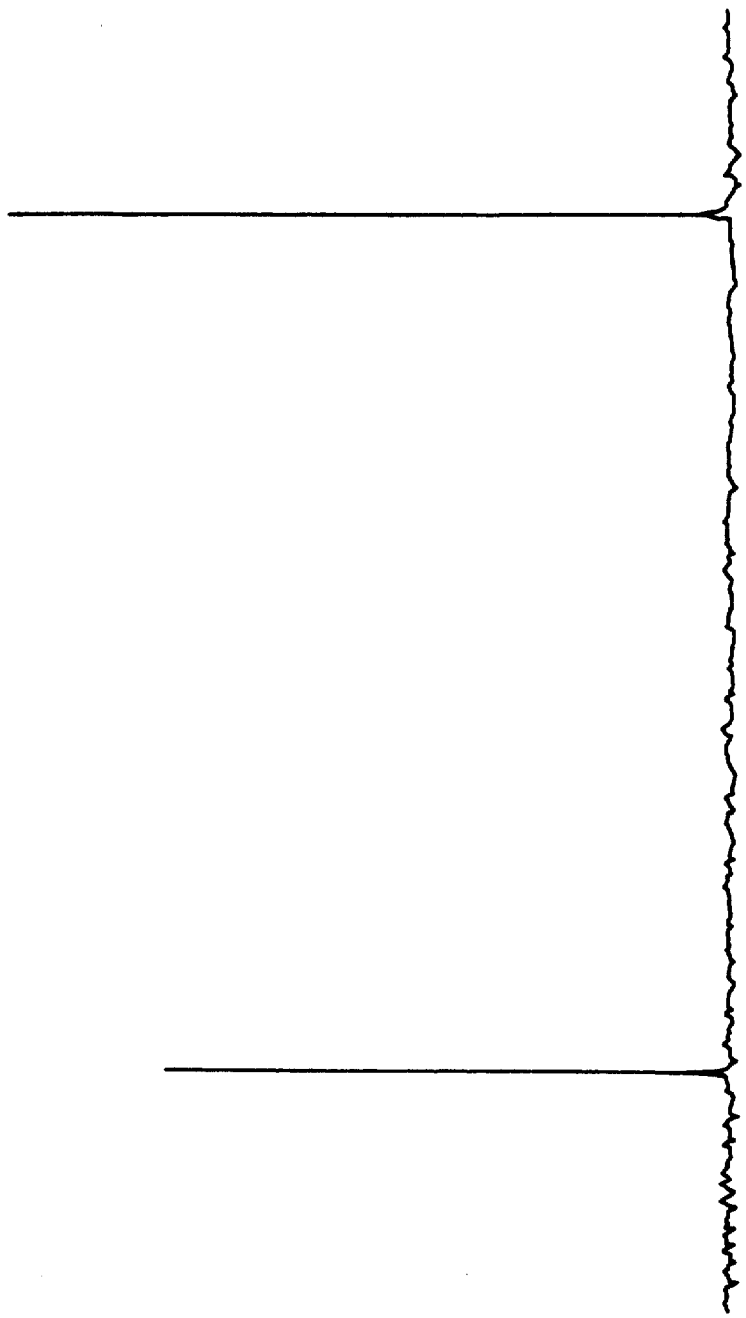
FIG. 3 is a $^{13}$C-NMR chart of glycine obtained in Example 1-1.
Figure 4:
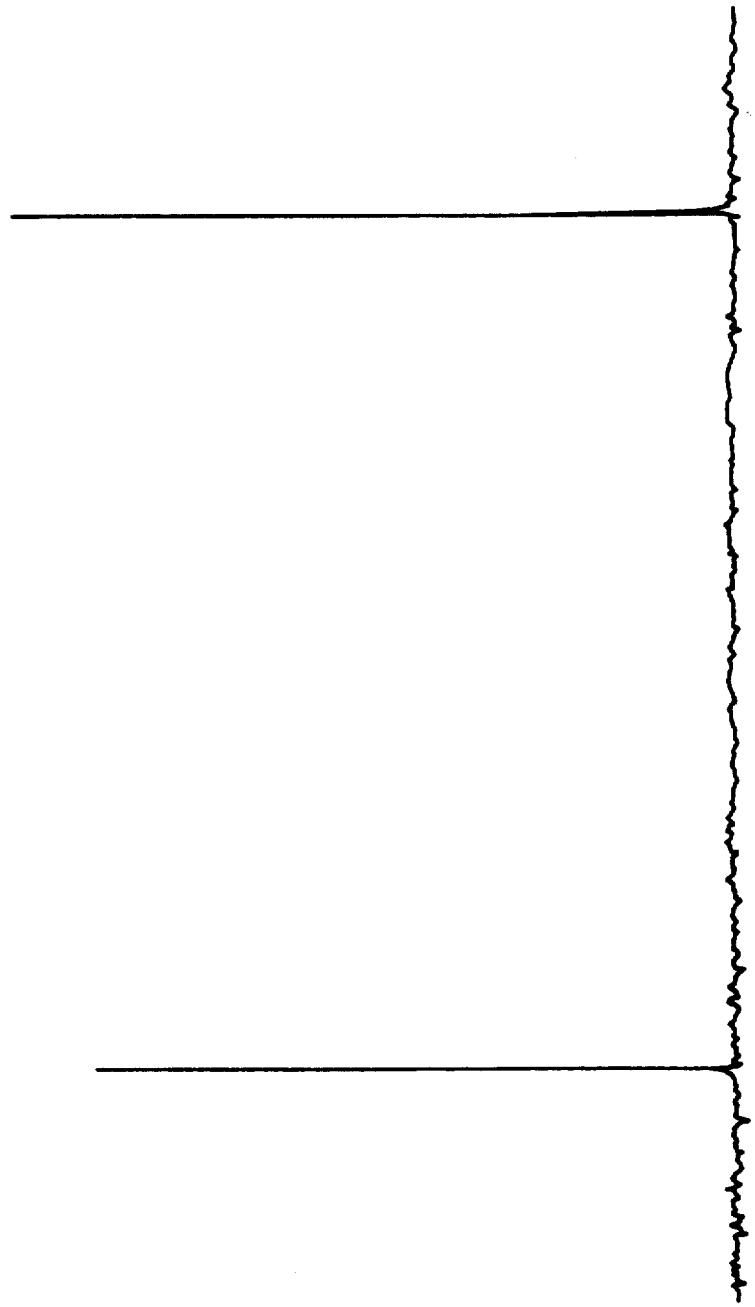
FIG. 4 is $^{13}$C-NMR chart of glycine obtained in Example 1-2.
Figure 5:
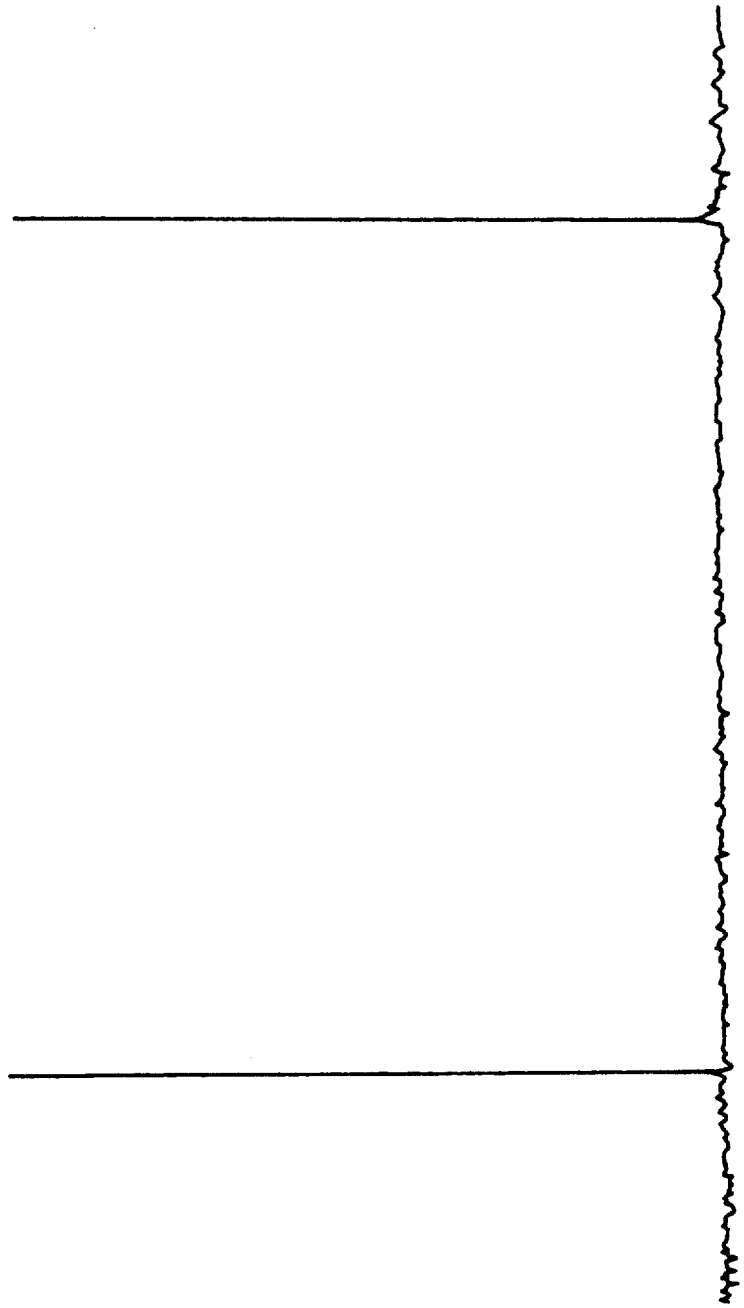
FIG. 5 is a $^{13}$C-NMR chart of standard glycine.

Results of $^{13}C$-NMR Measurement:

The same peek as that of the standard substance (see FIGS. 3 through 5).

Figure 6:
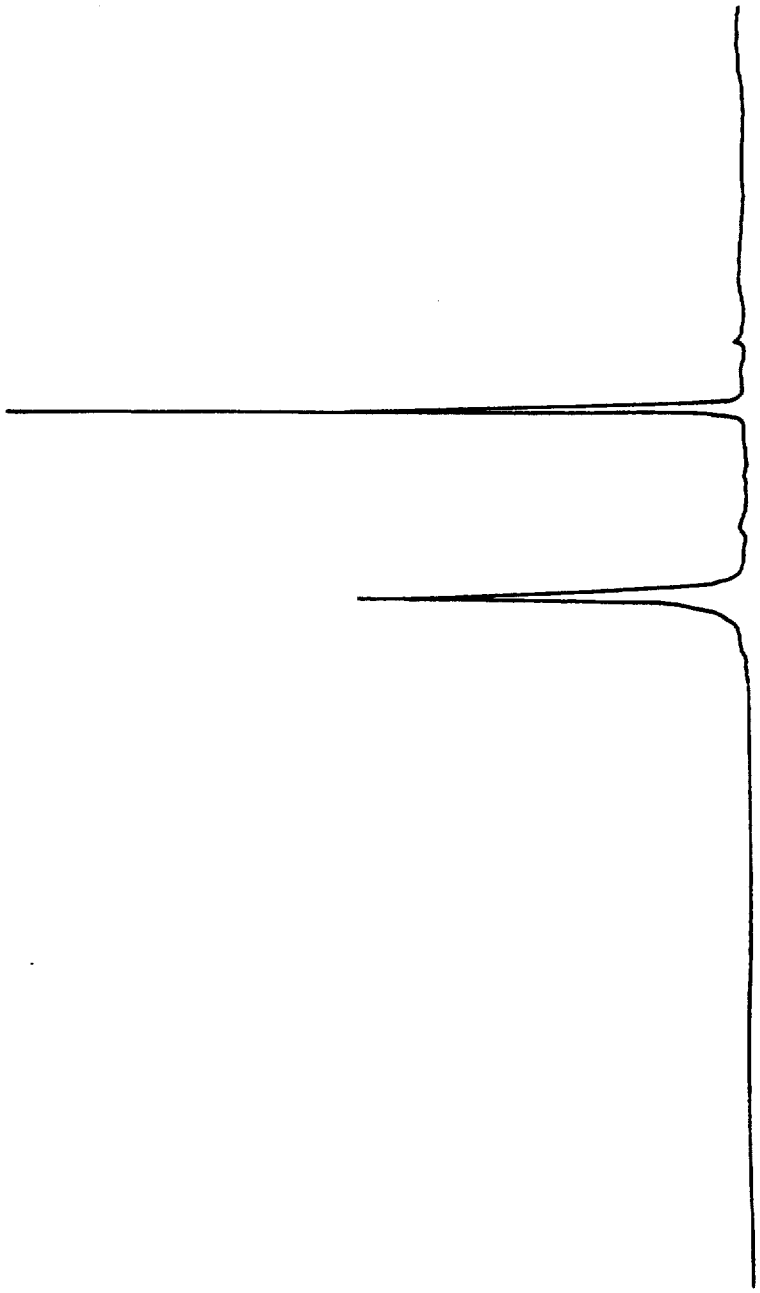
FIG. 6 is a $^1$H-NMR chart of glycine obtained in Example 1-1.
Figure 7:
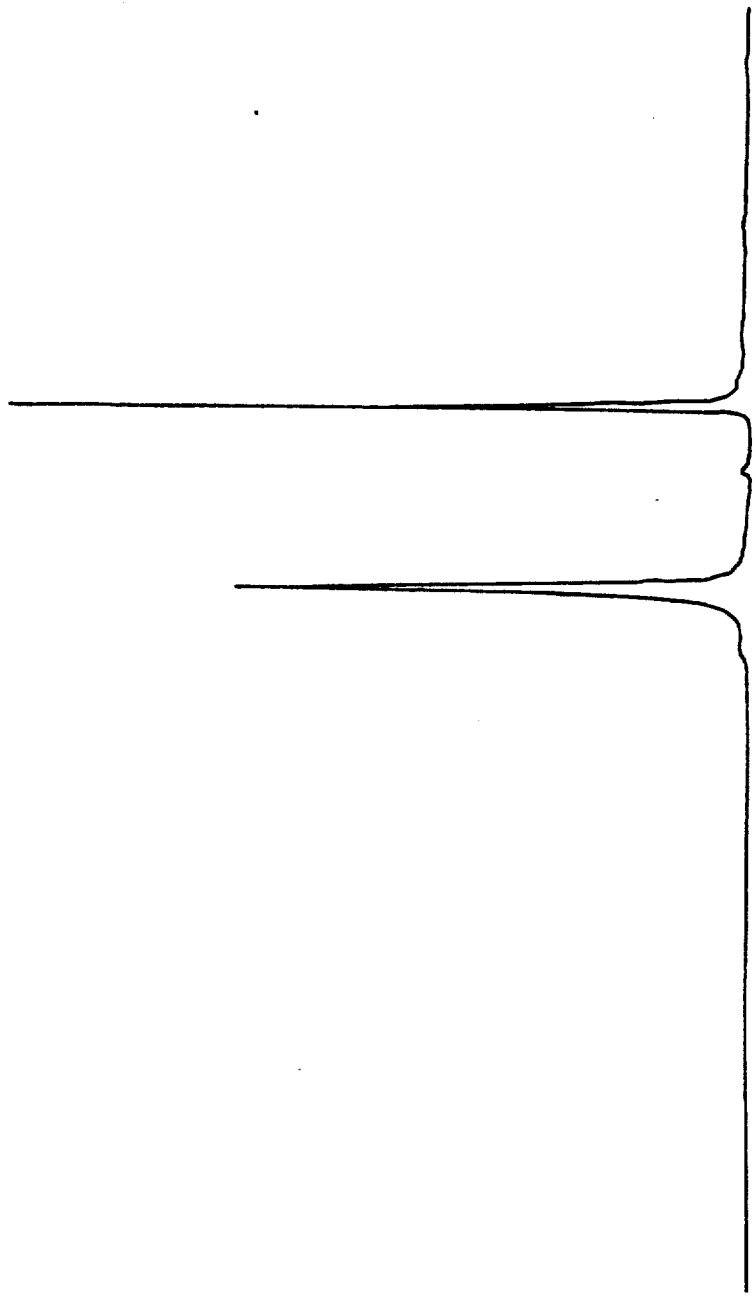
FIG. 7 is a $^1$H-NMR chart of glycine obtained in Example 1-2.
Figure 8:
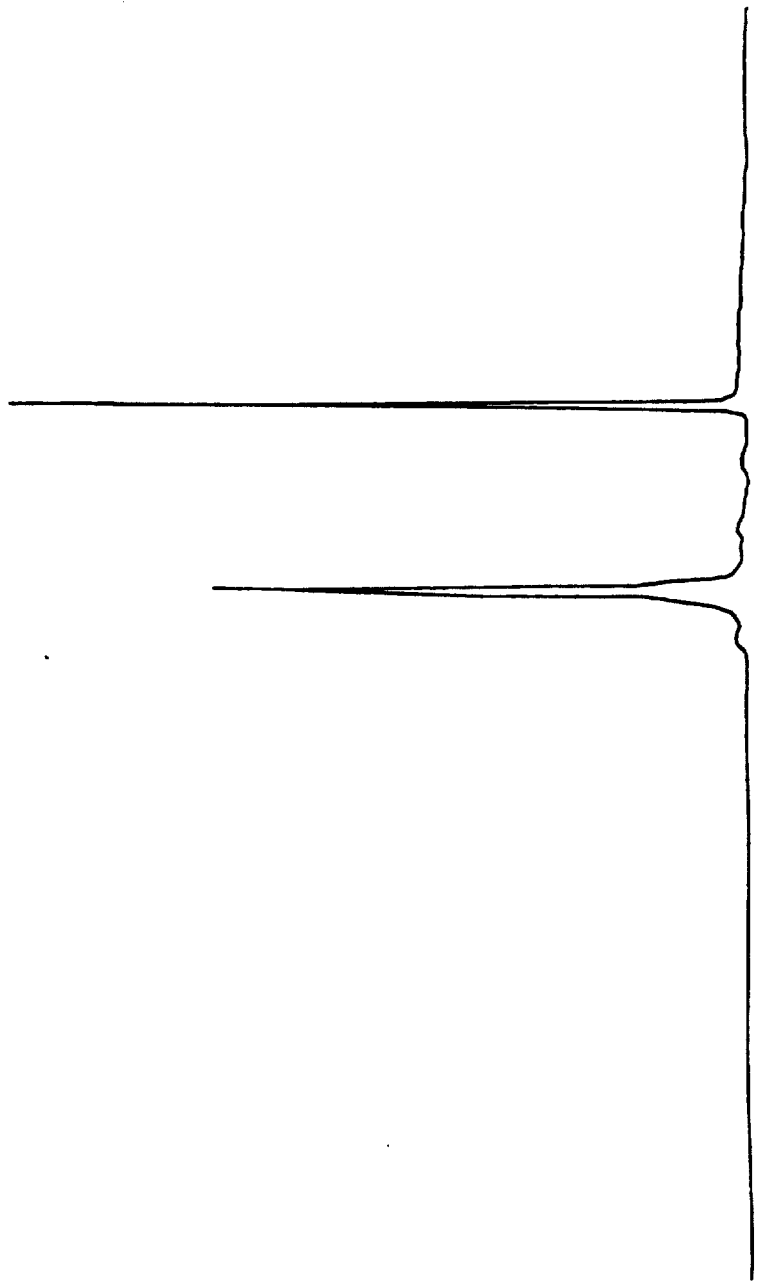
FIG. 8 is a $^1$H-NMR chart of standard glycine.

Results of $^1H$-NMR Measurement:

The same peek as that of the standard substance (see FIGS. 6 through 8).

Example 1-2

The reaction was carried out under the same conditions as described in Example 1-1 except that the reaction temperature was changed to 55° to 65° C. The following results were obtained.

Amount Obtained: 35.0 g.
Purity: 98.2% (titration method and HPLC).
Yield: 91.65%.
M.P.: 226° to 229 ° C. (decomposition started at 226° C.).

| Elementary Analysis Values: | | | |
|---|---|---|---|
| | C | H | N |
| Found values | 32.00 | 6.65 | 18.62 |
| Theoretical Value | 32.00 | 6.71 | 18.66 |

Results of IR Measurement: The same as obtained in Example 1-1.

Results of $^{13}C$-NMR Measurement: The same as obtained in Example 1-1.

Results of $^1H$-NMR Measurement: The same as obtained in Example 1-1.

Example 1-3

In 100 cc of methanol was suspended 22.5 g (0.75 mole) of paraformaldehyde, and 19 g of ammonia gas was passed through the slurry solution and supply of ammonia gas was stopped when the liquid became in clear. The temperature was maintained at 20° C. during the introduction of ammonia gas.

Separately, 47.25 g (0.5 mole) of monochloroacetic acid was dissolved in 100 cc of methanol, and when 50.50 g (0.5 mole) of triethylamine was added to the solution, exothermic reaction was caused. The methanol solution of the aminomethanol derivative formed by the above reaction of paraformaldehyde and ammonia was added to the reaction liquid while maintaining the final temperature at 60° C. The mixture was stirred and reacted at 60°±2 ° C., and the reaction was stopped when the disappearance of the peak of monochloroacetic acid was confirmed by HPLC. The time required for the reaction was about 3 hours. While the formed slurry reaction liquid was still warm, the reaction liquid was two times rinsed with 20 cc of warm water and was washed and dried to obtain a white crystalline powder.

Amount Obtained: 35.0 mg.
Purity: 98.7% (titration method and HPLC method).
Yield: 92.12%.
M.P.: 226° to 229 ° C. (decomposition started at 226° C.).

Results of I.R., $^{13}C$-NMR and $^1H$-NMR Measurements: The same as obtained in Example 1-1.

Example 1-4

The reaction was carried out under the same of tributylamine (0.5 mole; purity of 98.5%) was used instead of 50.5 g (0.5 mole) of triethylamine. The following results were obtained.

Amount Obtained: 34.8 g.
Purity: 98.6% (titration method and HPLC).
Yield: 91.50%.
M.P.: 226.1° to 229.0 ° C. (with decomposition).

Examples 1-5 through 1-7

The test was carried out in the same manner as described in Example 1-3 by using ethanol, propanol and n-butanol as the solvent. The obtained amounts, purities, yields and melting points were as shown below.

TABLE 1

| | Example No. | | |
|---|---|---|---|
| | 1-5 | 1-6 | 1-7 |
| Solvent | ethanol | propanol | n-butanol |
| Obtained Amount (g) | 35.2 | 34.0 | 34.5 |
| Purity (%) | 98.9 | 98.4 | 98.2 |
| Yield (%) | 92.83 | 90.53 | 90.34 |
| M.P. (°C.) | 226.3–229.0 | 226.2–229.0 | 226–229 |

Example 1-8

In 100 cc of ethanol was suspended 22.5 g (0.75 mole) of paraformaldehyde, and 19 g of ammonia gas was passed through the suspension. The liquid became in clear, and the peak of the aminomethanol derivative was confirmed by HPLC.

In 200 cc of toluene was dissolved 47.25 g (0.5 mole) of monochloroacetic acid and 50.5 g (0.5 mole) of triethylamine was added to the solution. When the mixture was heated at about 100° C., a white precipitate was immediately formed. The precipitate was recovered by filtration and washed with ethanol. Carboxymethyl triethylammonium chloride was obtained substantially in the theoretical amount. The obtained chloride was dissolved in 150 cc of ethanol and the solution was maintained at 60° C., and when the above-mentioned ethanol solution of the aminomethanol derivative was added to the solution and the mixture was stirred, a turbid slurry was immediately formed. The reaction was completed within about 2 hours, and the reaction mixture was filtered and the recovered precipitate was rinsed two times with 20 cc of warm methanol and was washed and dried.

Amount Obtained: 35.2 g.
Purity: 98.6% (titration method and HPLC method).
Yield: 92.55%.
M.P.: 226.3° to 229 ° C. (with decomposition).

| Elementary Anapysis Results: | | | |
|---|---|---|---|
| | C | H | N |
| Found values | 32.00 | 6.70 | 18.66 |
| Theoretical Value | 32.00 | 6.70 | 18.66 |

Example 1-9

The test was carried out in the same manner as described in Example 1-3 except that methanol was used instead of ethanol and 72.5 g (0.5 mole) of tripropylamine was used instead of triethylamine.

Obtained Amount: 34.8 g.
Purity: 98.6% (titration method and HPLC method).
Yield: 91.5%.
M.P. 226.5° to 229.3 ° C. (with decomposition).

| Elementary Anapysis Results: | | | |
|---|---|---|---|
| | C | H | N |
| Found values | 32.03 | 6.70 | 18.66 |
| Theoretical Value | 32.00 | 6.70 | 18.66 |

Example 1-10

In 100 cc of ethanol having a water content of 30% was suspended 22.5 g (0.75 mole) of paraformaldehyde, and 19 g of ammonia was passed through the suspension at a temperature lower than 20° C. When the liquid became transparent, the reaction was stopped. Then, 47.25 g of monochloroacetic acid was dissolved in 150 cc of ethanol containing 30% of water, and 50.5 g of triethylamine was added to the solution and the mixture was stirred and reacted at 60° C. The above-mentioned solution of the aminomethanol derivative formed by the reaction between paraformaldehyde and ammonia was added to the reaction liquid, and the mixture was stirred and reacted at 60°±2° C. When the disappearance of the peak of monochloroacetic acid was confirmed by HPLC, the reaction was stopped. The obtained slurry was filtered at normal temperature to obtain a white crystal.

Amount Obtained: 33.6 g.
Purity: 98.5% (titration and HPLC).
Yield: 88.25%.
M.P. 226.2° to 229° C. (with decomposition).

Example 1-11

Into 100 cc of methanol were added 47.5 g (0.5 mole) of MCA and 50.5 g (0.5 mole) of triethylamine and the reaction was carried out at 60° C. Then, 22.5 g (0.75 mole) of paraformaldehyde was added to the reaction mixture and 23 g of ammonia was passed through the mixture. The temperature was maintained at 60°±2° C., and the reaction was completed within about 1.5 hours. The completion of the reaction was confirmed by HPLC. The formed precipitate of glycine was recovered by filtration at 40° to 50° C., and the precipitate was rinsed two times with warm methanol and was washed and dried to obtain glycine. The following results were obtained.

Obtained Amount: 37.0 g.
Purity: 98.5% (titration method and HPLC method).
Yield: 97.18%.
M.P.: 226.32° to 229.0 ° C.

Example 1-12

Into 100 cc of methanol were added 47.5 g (0.5 mole) of MCA and 50.5 g (0.5 mole) of triethylamine and the reaction was carried out at 60° C., and 26 g of the aminomethanol derivative recovered by cooling the filtrate left after recovery of glycine in Example 1-11 to −3° C. and recovering the precipitated crystal by filtration (comprising about 45% of paraformaldehyde and about 50% of the aminomethanol derivative) was added into the above MCA reaction liquid and 2.2 mg of paraformaldehyde was further added. Then, 22 g of ammonia gas was passed through the liquid mixture and the reaction was carried out at 60° C. for about 2 hours. After confirmation of the disappearance of the peak of MCA by HPLC, the reaction was stopped, and the reaction mixture was immediately filtered and the precipitate was rinsed with warm methanol, washed and dried to obtain glycine. The following results were obtained.

Obtained Amount: 36 g.
Purity: 98.6% (titration method and HPLC method).
Yield: 94.65%.
M.P.: 226.32° to 229° C. (with decomposition).

Example 2-1

In 50 cc of water was dissolved 47.25 g (0.5 mole) of MCA, and 52 g (0.52 mole) of triethylamine was dropped into the solution from a dropping funnel of a three-neck flask (equipped with a reflux condenser having a capacity of 500 cc, a thermometer and the dropping funnel and placed on a magnetic stirrer). When the mixture was stirred at room temperature, heat was automatically generated and the temperature was gradually elevated. While the temperature was maintained at 60° C. on a water bath, dropping of triethylamine was completed. Then, the temperature was elevated to about 70° C. and stirring was conducted for 30 minutes to complete the reaction of forming a carboxymethyl quaternary ammonium chloride. The obtained liquid is designated as "liquid A".

Separately, 60.7 g of 28% aqueous ammonia [containing 17 g (10 moles) of NH$_3$] was charged in a three-neck flask having a structure similar to that of the above-mentioned flask, and 61.6 g of 37% formalin liquid containing 22.5 g (0.75 mole) of HCHO was dropped into the flask from the dropping funnel. The temperature was maintained at or below 20° C., and the mixture was stirred. Formation of the aminomonomethanol derivative was confirmed by HPLC. The formed liquid is designated as "liquid B".

When the liquid B was dropped into the liquid A at room temperature, the temperature was gradually elevated. Accordingly, the temperature was controlled to 40° C. on a water bath. After completion of the dropping, the mixture was stirred at a temperature maintained at 40° C. The reaction was completed within about 3 hours. Complete disappearance of the peak of MCA was confirmed by HPLC, and not only the peak of glycine but also the peak of a methylene-imine compound formed by dehydration of the aminomonodimethanol, aminodimethanol and aminotrimethanol derivatives was observed on the HPLC chart.

Any peak of iminodiacetic acid or nitrilotriacetic acid was not observed.

The amount converted to glycine and the conversion, calculated by comparison with data of the standard substance of glycine, were 39.6 g and 97.6%, respectively.

Examples 2-2 through 2-4

The procedures of Example 2-1 were repeated in same manner except that the temperature for the reaction between the liquids A and B was changed to 50°, 60° and 70 ° C. The amounts of formed glycine and iminodiacetic acid were as shown in Table 2.

TABLE 2

| Example No. | Reaction Temperature (°C) | Reaction Time (minutes) | Amount (g) of Formed Glycine | Conversion (%) to Glycine | Amount (g) of Formed Iminodiacetic Acid |
| --- | --- | --- | --- | --- | --- |
| 2-2 | 50 | 120 | 36.2 | 96.53 | 0.6 |
| 2-3 | 60 | 60 | 35.4 | 94.40 | 1.2 |
| 2-4 | 70 | 30 | 34.7 | 92.00 | 2.0 |

Examples 2-5 and 2-6

The procedures of Example 2-1 were repeated in the same manner except that 0.52 mole of tripropylamine and 0.52 mole of tributylamine were used independently instead of 0.52 mole of triethylamine and the reaction temperature was changed to 40° C. in the former case or to 50° C. in the latter case. The obtained results are shown in Table 3.

TABLE 3

| Example No. | Tertiary Amine | Reaction Temperature (°C) | Reaction Time (minutes) | Amount (g) of Formed Glycine | Conversion (%) to Glycine | Amount (%) of Formed Iminodiacetic Acid |
| --- | --- | --- | --- | --- | --- | --- |
| 2-5 | tripropylamine | 40 | 180 | 36.5 | 97.3 | — |
| 2-6 | tributylamine | 50 | 90 | 36.0 | 96.0 | 0.5 |

Example 2-7

The procedures of Example 2-1 were repeated in the same manner except that in the liquid B, the aqueous ammonia/formalin molar ratio was changed to 0.75/0.6 or 1.25/1.0 while the amounts of MCA, triethylamine and water in the liquid A were not changed, and that the mixture of the liquids A and B was maintained at 50° C. The obtained results are shown in Table 4.

Example 2-11

At the same starting material ratio and reaction temperature (40° C.) as adopted in Example 2-1, the reaction was carried out under an inner pressure of 5 kg/cm$^2$ by N$_2$ gas purging (a stainless steel reactor having a capacity of 1000 cc was heated on a magnetic stirrer). The reaction time was 1.5 hours. The amount obtained of glycine was 36.5 g and the conversion to glycine was 97.3%.

Example 2-12

A liquid A was prepared by heating 47.25 g (0.5 mole) of MCA, 70 g of water and 0.52 mole of tripropylamine to form a carboxymethyl quaternary ammonium chloride.

A liquid B was prepared by reacting 39.47 g (0.5 mole) of a 38% formalin solution with 50 g of 28%

TABLE 4

| Example No. | Amount (g) of 28% Aqueous Ammonia | Amount (g) of 37% Formalin Liquid | Reaction Temperature (°C) | Reaction Time (minutes) | Amount (g) of Formed Glycine | Conversion (%) to Glycine | Amount (g) of Iminodiacetic Acid |
| --- | --- | --- | --- | --- | --- | --- | --- |
| 2-7 | 45.58 | 75.89 | 50 | 120 | 36.0 | 96.0 | 1.0 |
| 2-8 | 48.65 | 81.08 | 50 | 90 | 36.2 | 29.35 | 0.9 |

Examples 2-9 and 2-10

Reaction between liquids A and B described below was carried out at 70 or 80° C. The obtained results are shown in Table 5.

Liquid A

A carboxymethyl quaternary ammonium chloride solution was prepared by reacting 47.25 g (0.5 mole) of MCA, 52 mg of triethylamine and 0 cc of water at 60° C.

Liquid B

A liquid was prepared by mixing 28% aqueous ammonia with formalin liquid at a molar ratio of 0.75/0.6, that is, a weight ratio of 45.58 g/75.89 g.

aqueous ammonia at 20° C. to form an aminomethanol derivative. The liquids A and B were charged at a molar ratio of 0.5/0.77 in a three-neck flask having capacity of 500 cc and the mixture was maintained at 50° C. for 10 minutes. Then, 20 g of 28% aqueous ammonia was added dropwise into the flask over a period of 10 minutes. The mixture was maintained at 50° to 55° C. for 30 minutes to complete the reaction. During the reaction, the pH value was maintained at 10.0. By the calculation from the results of the HPLC examination, it was confirmed that 36.8 g of glycine was formed by the reaction conducted for about 50 minutes.

The peak of iminodiacetic acid was not found in HPLC chart. The conversion to glycine was 98.13%.

Example 2-13

To a suspension of 22.5 g (0.75 mole) of paraformaldehyde in 36.7 cc of water was added 71.0 g of 28%

TABLE 5

| Example No. | Amount (g) of 28% Aqueous Ammonia | Amount (g) of 37% Formalin Liquid | Reaction Temperature (°C) | Reaction Time (minutes) | Amount (g) of Formed Glycine | Conversion (%) of Glycine | Amount (g) of Formed Iminodiacetic Acid |
| --- | --- | --- | --- | --- | --- | --- | --- |
| 2-9 | 45.58 | 75.89 | 70 | 30 | 34.5 | 92.0 | 2.2 |
| 2-10 | 45.58 | 75.89 | 80 | 15 | 33.6 | 89.6 | 3.1 | aqueous ammonia [19.88 g (1.17 moles) of NH₃] dropwise and reaction was carried out at a temperature maintained at 20° C. to form an aminomethanol derivative solution. The obtained solution is designated as "liquid A".

In 50 cc of water was dissolved 47.25 g of MCA, and g of triethylamine was dropped into the solution to obtain "liquid B".

The apparatus and method adopted for forming the liquids A and B were the same as those described in Example 2-1.

In the same manner as described in Example 2-1, the liquids A and B were reacted at 50° C. The reaction was completed for about 2 hours.

The amount of obtained glycine was 36.5 g and the conversion to glycine was 97.3%. Formation of iminodiacetic acid was not confirmed.

Example 3-1 (Continuous Reaction)

A compact roll of a tightly wound 100-mesh stainless steel net was compactly filled in a stainless steel pipe having an inner diameter of 22 mm, an outer diameter of 25 mm and a length of 2 m, and the periphery of the pipe was covered with an asbestos-coated nichrome wire heater and a temperature adjuster was attached thereto. A distributor having 40-mesh fine holes uniformly arranged was attached to the top of the pipe. The following liquids were prepared.

Liquid A

In 700 cc of water was dissolved 472.5 g (5 moles) of MCA, and the aqueous solution was reacted with 520 g (5.2 moles) of triethylamine to obtain 1420 cc of an aqueous solution of a carboxymethyl ammonium chloride.

Liquid B

With 455.4 g of 28% aqueous ammonia [containing 127.5 g (7.5 moles) of NH₃] was reacted 486.5 g of 37% formalin liquid [containing 180 g (6 moles) of HCHO] to obtain 942 cc of an aminomethanol derivative.

The reaction pipe was heated at 80° C. in advance and when the temperature became stable, the liquids A and B were supplied as fine streams into the distributor at flow rates of 71 cc/min and 47.1 cc/min, respectively, to mix both the liquids. The liquid mixture was let to fall down on the 100-mesh net uniformly through the 40-mesh holes. About 6 minutes were necessary for the mixture to flow out through the 100-mesh net.

When the effluent was examined by HPLC, it was confirmed that the glycine content was 15.45% W/V, the total glycine amount was 365 g and the conversion to glycine was 97.33% based on MCA. Formation of iminodiacetic acid was not confirmed.

The aminomethanol derivative was substantially converted to the dimethyl derivative, though formation of a small amount of the trimethyl derivative was confirmed.

I claim:

1. A process for preparing glycine in a high yield, which comprises reacting a carboxymethyl quaternary ammonium chloride represented by the following structural formula (I):

$$Cl(R_3NCH_2COOH) \tag{I}$$

wherein R represents an alkyl group having 1 to 4 carbon atoms,
with an aminomethanol derivative represented by the following structural formula (II):

$$\underset{HO.CH_2NH}{\overset{R_1}{|}} \tag{II}$$

wherein R₁ represents a hydrogen atom or a CH₂OH group,
in a solvent.

2. A process for preparing glycine according to claim 1, wherein the reaction is carried under atmospheric pressure or elevated pressure and at a temperature lower than the boiling point of the solvent under the reaction pressure.

3. A process for preparing glycine according to claim 1, wherein the solvent is an aqueous solvent.

4. A process for preparing glycine according to claim 1, wherein the solvent is an alkyl alcohol type solvent.

5. A process for preparing glycine according to claim 4, wherein the alkyl alcohol type solvent is a lower alcohol having 1 to 4 carbon atoms.

6. A process for preparing glycine according to claim 1 or 2, wherein the solvent is the mixture of alkyl alcohol and water in 40% w/w or below water content.

7. A process for preparing glycine according to claim 1 or 2, wherein a reaction product formed by reacting monochloroacetic acid with a tertiary amine having 1 to 4 carbon atoms in water or an inert organic solvent is used as the carboxymethyl quaternary ammonium chloride.

8. A process for preparing glycine according to claim 1, wherein a reaction product formed by reacting ammonia with formalin or paraformaldehyde is used as the derivative.

9. A process for preparing glycine according to claim 8, wherein the reaction of ammonia with formalin or paraformaldehyde is carried out at a temperature lower than 50° C.

10. A process for preparing glycine according to claim 9, wherein the reaction of ammonia with formalin is carried out in an aqueous solvent at a pH value of at least 9.

11. A process for preparing glycine according to claim 1, wherein the aminomethanol derivative is reacted in an amount of 1.0 to 2.0 moles per mole of the carboxymethyl quaternary ammonium chloride.

* * * * *